United States Patent [19]

Bakhshaei

[11] Patent Number: 5,148,826
[45] Date of Patent: Sep. 22, 1992

[54] MOISTURE MONITORING AND CONTROL SYSTEM

[76] Inventor: Behrooz Bakhshaei, 26831 Anadale Dr., Laguna Hills, Calif. 92653

[21] Appl. No.: 753,782

[22] Filed: Sep. 3, 1991

[51] Int. Cl.$^5$ .............................................. A01G 25/16
[52] U.S. Cl. ...................................... 137/80; 137/78.3; 239/64
[58] Field of Search .................... 137/78.3, 79, 80; 239/63, 64

[56] References Cited

U.S. PATENT DOCUMENTS

| | | | |
|---|---|---|---|
| 2,906,952 | 9/1959 | Horecky | 239/63 |
| 3,590,335 | 6/1971 | Tetar | 239/64 |
| 3,771,548 | 11/1973 | Rauchwerger | 137/78.3 |
| 3,991,375 | 11/1976 | Riggs et al. | 239/64 |
| 4,197,866 | 4/1980 | Neal | 137/78.3 |
| 4,216,789 | 8/1980 | Hasenbeck | 239/63 |
| 4,333,490 | 6/1982 | Enter, Jr. | 137/80 |
| 4,541,563 | 9/1985 | Uetsuhara | 239/64 |
| 4,545,396 | 10/1985 | Miller et al. | 137/78.3 |
| 4,693,419 | 9/1987 | Weintraub et al. | 239/63 |
| 4,796,654 | 1/1989 | Simpson | 137/78.3 |
| 4,850,386 | 7/1989 | Bireley | 137/78.3 |
| 4,892,113 | 1/1990 | Fattahi | 137/78.3 |

FOREIGN PATENT DOCUMENTS 600749 6/1977 Switzerland ........................ 239/63

*Primary Examiner*—A. Michael Chambers

[57] ABSTRACT

There is provided a system for monitoring moisture level in soil and controlling application of water to the soil. The system includes a moisture level sensor which generates a small voltage through the Volta effect. This voltage is amplified and is then used to trigger a switch typically connected to a standard watering timer. The sensor signal may be compared to a present voltage level through a comparator, and in this way the amount of moisture in the soil which will determine the "on" condition can be selected. The preferred sensor in the present invention is a bimetallic element, the soil functioning as an electrolyte in contact with the bimetallic element such that a Volta effect electromotive force is produced in the bimetallic element. A temperature sensor is also included, and functions in parallel to the moisture sensor such that both moisture level and temperature level must be within a present range in order for the comparator to pass an output signal on to the switch. Multiple sensors may be used in a configuration that allows each sensor or pair of sensors to control one set of watering devices so that various preconditions may be set for different zones of soil to be watered.

4 Claims, 4 Drawing Sheets

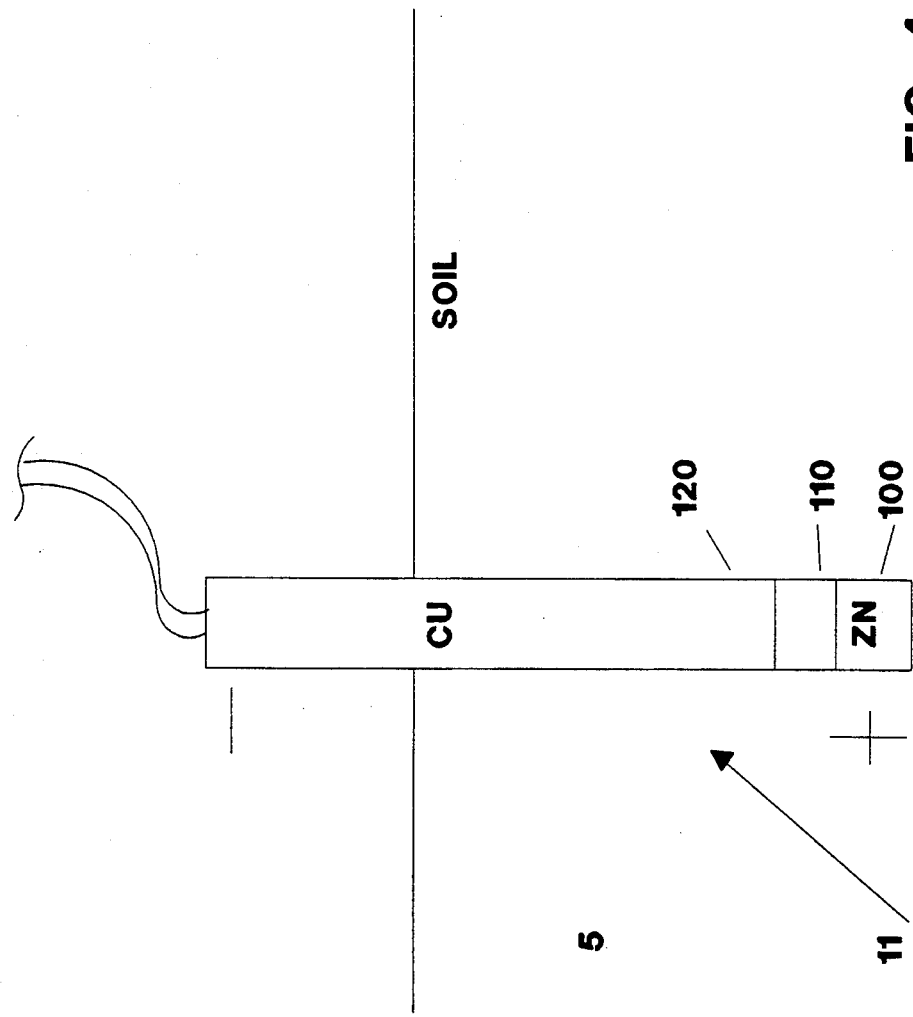

MOISTURE MONITORING AND CONTROL SYSTEM

FIELD OF THE INVENTION

This invention relates to water sprinkler control systems and, more particularly, to a control system that monitors soil moisture levels and air temperature to optimize use of water.

BACKGROUND OF THE INVENTION

It is becoming increasingly more important to monitor the use of water in many sectors of society. As such, a variety of sprinkler controller systems are available that permit watering of vegetation only when soil moisture levels fall below a predetermined level. For example, U.S. Pat. No. 4,892,113 to Fattahi on Jan. 9, 1990 discloses such a system.

Currently available monitoring and control systems do not take into account air temperature as an important parameter in actuation of irrigation systems. For example, if air temperature is below 32° F., current systems will still permit the actuation of irrigation systems. Moreover, if air temperature is high enough, watering vegetation will result in a high degree of evaporation. Consequently, there is a strong need for an irrigation control system that utilizes soil moisture levels and air temperature to determine optimal temperature and soil moisture levels for irrigation.

Currently available monitoring and control systems are also unnecessarily complex, requiring an external power source for moisture detectors. Moreover, many currently available monitoring and control systems require the use of alternating current, due to capacitive moisture sensoring techniques, which further add to the complexity and costs of such systems.

Clearly, then, a moisture monitoring and sprinkler control system is needed that not only inhibits actuation of the watering system when soil moisture is sufficient, but also inhibits actuation of the watering system when the air temperature is not within a specified range. Such a needed system would not require external power to the moisture sensors, and would function on DC voltages, thereby reducing complexity and cost of the system. The present invention fulfills these needs and provides further related advantages.

SUMMARY OF THE INVENTION

In accordance with the present invention there is provided a system for monitoring moisture level in soil and controlling application of water to the soil such as in a garden, a lawn or other foliage requiring a scheduled maintenance of watering. As used herein the term soil shall include any sort of earth useful for growing vegetation such as ordinary soil, sand, gravel, rockwool, consolidated aggregate of any sort, and man made or manufactured materials of a wide variety which support the growth of vegetation. The system includes a moisture level sensor which generates a small voltage through the Volta effect. This voltage is amplified and is then used to trigger a switch typically connected to a standard watering timer. The sensor signal may be compared to a preset voltage level through a comparator, and in this way the amount of moisture in the soil which will determine the "on" condition can be predetermined. The preferred sensor in the present invention is a bimetallic element, the soil functioning as an electrolyte in contact with the bimetallic element such that a Volta effect electromotive force is produced in the bimetallic element. One possibility for the bimetallic element is a copper electrode and a zinc electrode, the two electrodes being separated by an insulator. The present invention may also include a temperature sensor which functions in parallel with the moisture sensor such that both moisture level and temperature level must be within a present range in order for the comparator to pass an output signal on to the switch. Typically, either a thermistor or a transistor may be used as the temperature sensing device. The system described above may be used with multiple sensors in a configuration that allows each sensor or pair of sensors to control one set of watering devices so that various preconditions may be set for different zones. Because the system takes into account the actual need for water based on the moisture level requirement in the soil and also the outside temperature, the amount of water actually needed by a garden or lawn is supplied without wasting water and without underwatering of the foliage. In this way the system takes into account rainy days, overcast days, cold days in which the amount of water evaporating from the soil is low, freezing days, plant watering needs, soil type, shade areas intermixed with sunny areas of the garden, and soil areas that receive water from other sources. A significant advantage of the present invention is that the moisture sensor does not require external power because the Volta effect produces a useful voltage between the dissimilar electrodes in proportion to the amount of moisture present in the soil. This voltage is amplified at the base station which is near a power source. Therefore less wiring and complexity of the circuitry is required. Another significant feature of the present invention is that it may be an all DC voltage system which, again, provides for less complexity and cost.

The system of the present invention is adapted to accurately monitor the moisture content in the soil on a continuous basis and control the proper watering of the soil through a watering means external to the invention. Accordingly, no water is supplied to the soil unless its moisture content is less than a present moisture level. Therefore water is conserved in that only the appropriate amount of water is actually delivered to the soil.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 4 is a cross-sectional view of a bimetallic element functioning as a moisture sensor embedded in soil.

DETAILED DESCRIPTION OF THE PREFERRED EMBODIMENT

Figure 1:
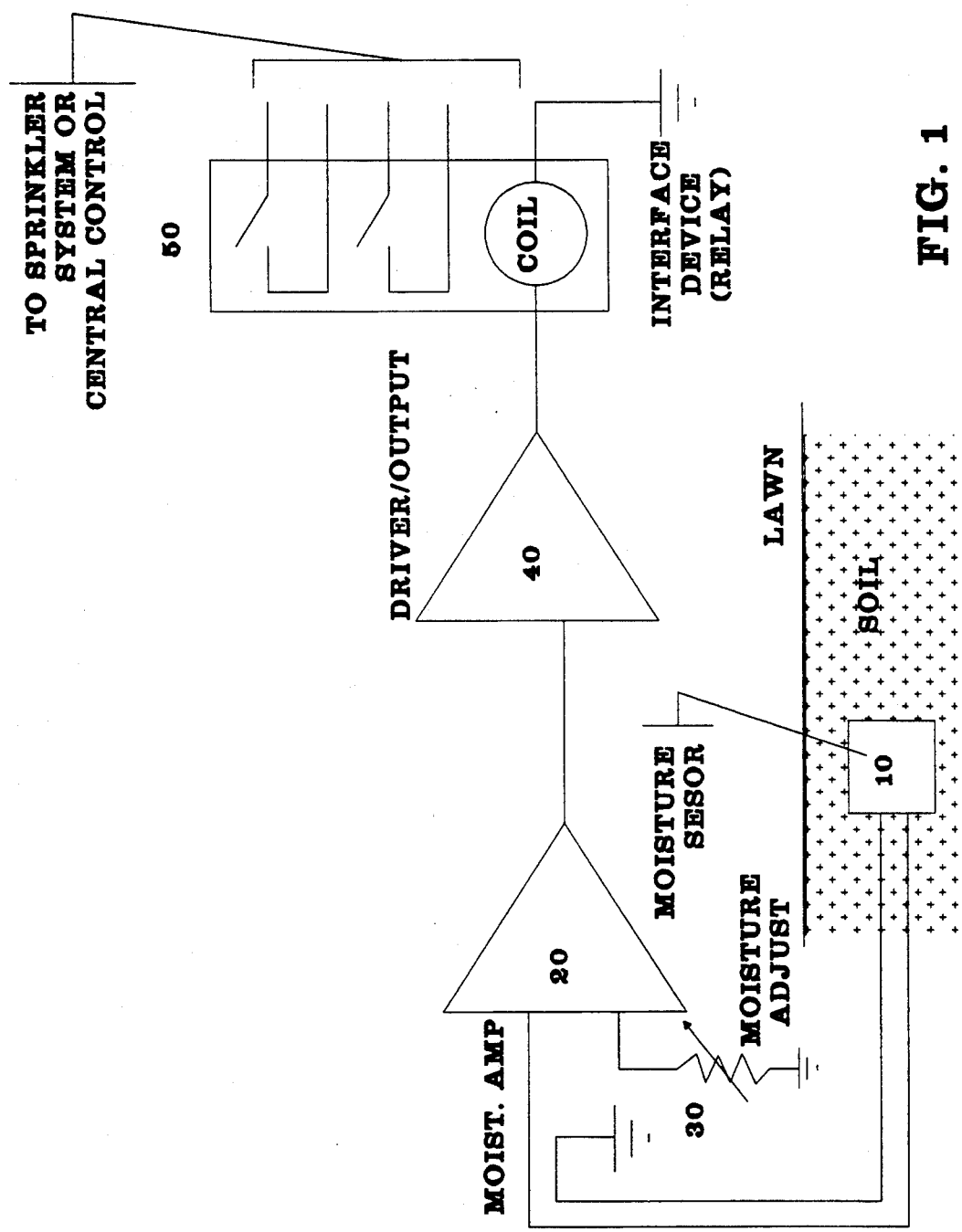
FIG. 1 is a schematic diagram of the invention, illustrating a moisture sensor, a pre-amplifier, a power amplifier, and a switching means.

FIG. 1 shows a system for monitoring moisture level in soil 5 and controlling the application of water to the soil 5. A moisture level sensing means 10 in the soil 5 is electrically interconnected with a pre-amplifier 20, which, in turn, is electrically interconnected with a power amplifier 40 that drives an electrical circuit switching means 50. The moisture level sensing means 10 is positioned in the soil 5 such that a first voltage proportional to the level of moisture in the soil 5 adjacent to the moisture level sensing means 10 is produced by the moisture level sensing means 10. The first voltage is amplified by the power amplifier 40 to a level adequate to energize the switching means 50, whereby the moisture level in the soil 5 is used to energize and to deenergize the switching means 50 in accordance with the moisture level in the soil 5.

Preferably, the moisture level sensing means 10 is a bimetallic element 11, such as a copper electrode 120 and a zinc electrode 100 separated by an insulator 110 (FIG. 4). In such an embodiment, the soil 5 functions as an electrolyte in contact with the bimetallic element 11 to produce a Volta effect electromotive force in the bimetallic element 11. This electromotive force produces the first voltage.

Figure 2:
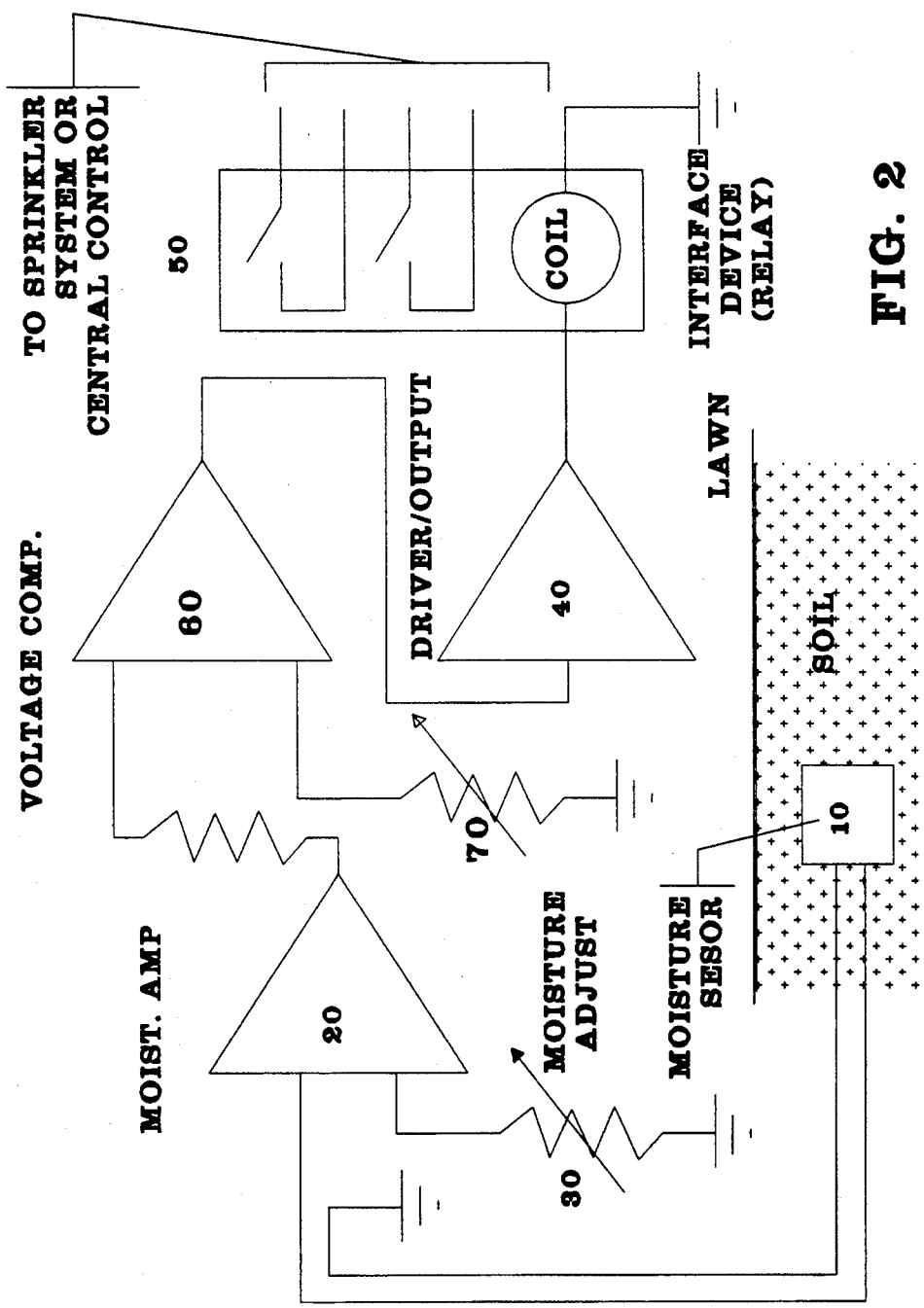
FIG. 2 is the schematic diagram of FIG. 1 further including a voltage comparator.

The preferred embodiment further includes a voltage comparator 60 (FIG. 2). The first voltage is conducted to the comparator 60, which is disposed between the moisture level sensing means 10 and the power amplifier 40. The first voltage is compared with a first base voltage. Preferably, the first base voltage is adjustable with a moisture adjustment means 30, whereby the level of soil moisture required for actuation of the switching means 50 is selectable. The comparator 60 produces a comparator output voltage only when the first voltage is larger in magnitude than the first base voltage.

Figure 3:
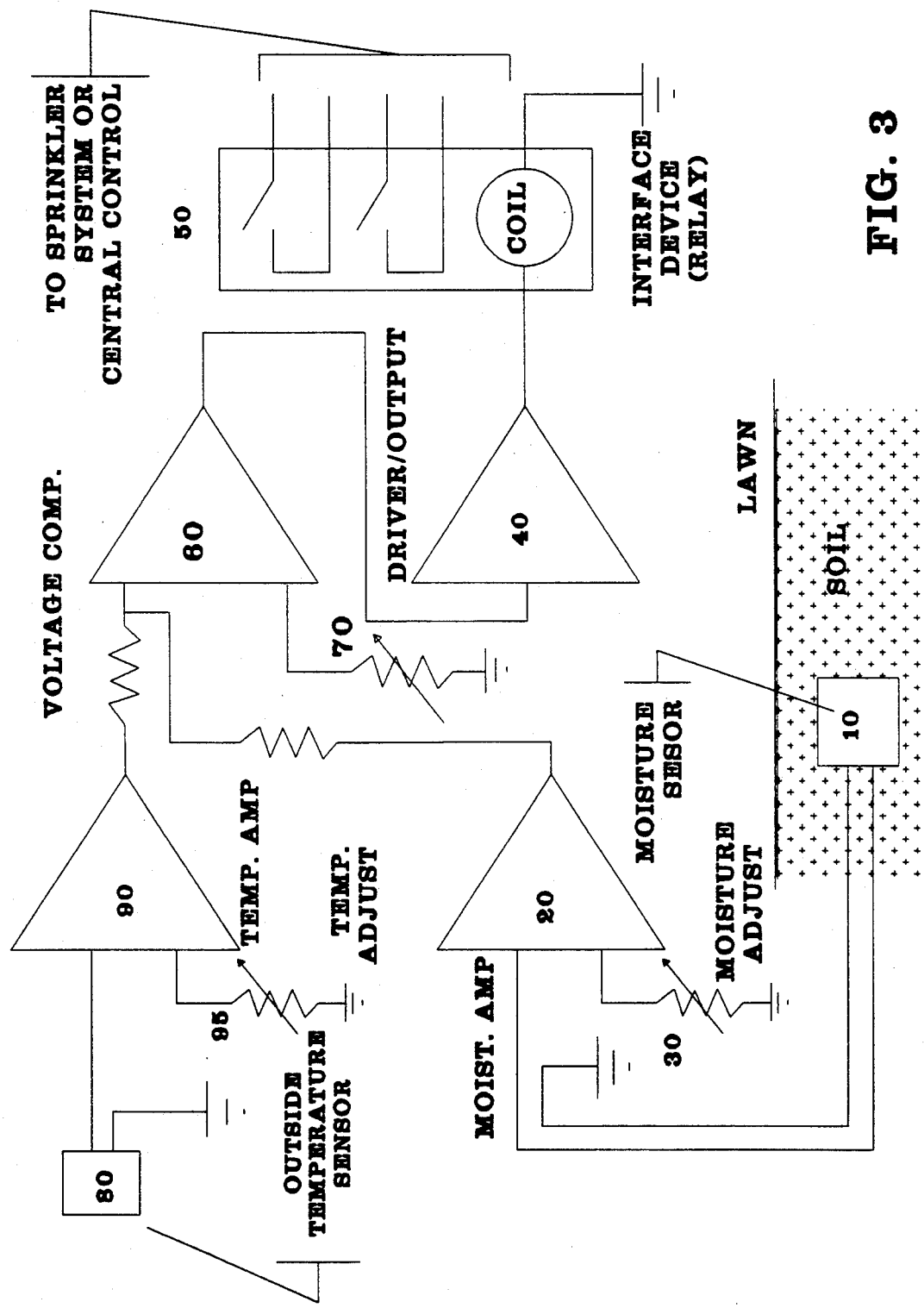
FIG. 3 is the schematic diagram of FIG. 2 further including an air temperature sensing means and a second pre-amplifier.

The preferred embodiment further includes an air temperature sensing means 80, such as a thermistor or a transistor, and a second pre-amplifier 90 (FIG. 3). The temperature sensing means 80 produces a second voltage that is proportional to the air temperature. The second voltage is conducted to the comparator 60, which is disposed between the air temperature sensing means 80 and the power amplifier 40. The second voltage is compared with a second base voltage. Preferably, the second base voltage is adjustable with a temperature adjustment means 95, whereby the level of air temperature required for actuation of the switching means 50 is selectable. The comparator 60 produces a comparator output voltage only when the first and the second voltages are stronger than the first base voltage and the second base voltage respectively. Preferably, the first and the second voltages, the first and the second base voltages, the comparator output voltage, and the pre-amplifier 20,90 output voltages are all DC voltages.

While the invention has been described with reference to a preferred embodiment, it is to be clearly understood by those skilled in the art that the invention is not limited thereto. For example, the system described above may be used with multiple sensors 10 and 80 in a configuration that allows each sensor or pair of sensors to control one set of watering devices so that various preconditions may be set for different zones of soil 5. Thus, the scope of the invention is to be interpreted only in conjunction with the appended claims.

I claim:

1. A system for monitoring moisture level in soil and controlling application of water to the soil, the system comprising:
    a plurality of a means for sensing moisture level in the soil at a plurality of discrete points, each said moisture level sensing means being electrically interconnected with one of;
    a plurality of power amplifiers, where each said power amplifier is electrically interconnected with one of;
    a plurality of a means for switching an electrical circuit; each of the moisture level sensing means is positioned in the soil such that a first voltage proportional to the level of moisture in the soil adjacent to each of the moisture level sensing means is produced by each of the moisture level sensing means, each of the first voltages being amplified by each one of the power amplifiers to a level adequate to energize each of the switching means whereby each of the moisture levels in the soil is used to energize and to deenergize each of the switching means in accordance with each of the moisture levels in the soil.

2. The system of claim 1 further including a plurality of a means for sensing air temperature and a plurality of voltage comparators, each of the temperature sensing means producing a second voltage, each of the second voltages being proportional to the air temperature, each of the second voltages conducted to each of the comparators, each of the comparators being disposed between each one of the moisture level sensing means and each one of the power amplifiers, such that each of the first and the second voltages are each compared with each of a first and a second base voltages respectively, each of the comparators producing a comparator output voltage only when each of the first and the second voltages are stronger than each of the first and the second base voltages respectively.

3. The system of claim 2 wherein each of the first and the second base voltages are adjustable whereby each of the levels of air temperature and each of the levels of soil moisture required for actuation of each of the switching means are each selectable.

4. A device for monitoring moisture in a soil for controlling the application of water to the soil, comprising:
    a bimetallic element having a first metallic electrode and a second metallic electrode, the electrodes separated by an insulator, the electrodes and the insulator forming a linear rod of such dimension as to be easily inserted into the soil, the electrodes being in contact with the soil, the rod having a conductor pair, one portion of the conductor pair extending from one end thereof, the conductor pair making electrical contact with the electrodes, the conductor pair for electrical interconnection of the electrodes with;
    a power amplifier, electrically interconnected with;
    a means for switching such that the soil functions as an electrolyte in contact with the electrodes to produce a Volta effect first voltage in the conductor pair, the first voltage being proportional to the level of moisture in the soil adjacent to the bimetallic element, the first voltage being amplified by the power amplifier to a level adequate to energize the switching means, whereby the moisture level in the soil is used to energize and to deenergize a means for soil watering.

* * * * *